United States Patent [19]

Willingham

[11] Patent Number: 5,242,893
[45] Date of Patent: Sep. 7, 1993

[54] USE OF HEXAMETHYLENETETRAMINE AS A STABILIZER FOR 3-ISOTHIAZOLONES

[75] Inventor: Gary L. Willingham, Glenside, Pa.

[73] Assignee: Rohm and Haas Company, Philadelphia, Pa.

[21] Appl. No.: 908,681

[22] Filed: Jul. 6, 1992

Related U.S. Application Data

[63] Continuation-in-part of Ser. No. 762,972, Sep. 20, 1991, abandoned, which is a continuation of Ser. No. 488,350, Mar. 2, 1990, abandoned.

[51] Int. Cl.$^5$ .............................................. A01N 43/80
[52] U.S. Cl. ................................... 504/138; 504/156; 514/244; 514/439; 514/445
[58] Field of Search .................. 514/439, 445, 244; 71/67; 504/138, 156

[56] References Cited

U.S. PATENT DOCUMENTS

| | | | |
|---|---|---|---|
| 3,523,121 | 8/1970 | Lewis et al. | 548/213 |
| 3,761,488 | 9/1973 | Lewis et al. | 548/213 |
| 3,870,795 | 3/1975 | Miller et al. | 514/372 |
| 4,067,878 | 1/1978 | Miller et al. | 548/213 |
| 4,129,448 | 12/1978 | Greenfield et al. | 106/15 |
| 4,150,026 | 4/1979 | Miller et al. | 548/101 |
| 4,165,318 | 8/1979 | Greenfield et al. | 252/380 |
| 4,241,214 | 12/1980 | Miller et al. | 548/101 |

FOREIGN PATENT DOCUMENTS

| | | |
|---|---|---|
| 46721 | 1/1978 | Hungary . |
| 153303 | 10/1979 | Japan . |
| 2138102 | 5/1990 | Japan . |

OTHER PUBLICATIONS

Tsunoda et al., CA 113: 128098g "Marine antifouling agents . . . " pub date 28 May 1990.
H. W. Rossmore & M. Sondossi "Advance in Applied Microbiology" 1988 (33, 230).

*Primary Examiner*—Allen J. Robinson
*Assistant Examiner*—B. Bembenick
*Attorney, Agent, or Firm*—Michael B. Fein

[57] ABSTRACT

Disclosed are the use of hexamethylenetetramine as a stabilizer for 3-isothiazolones under basic conditions, i.e. above pH 7.0, and compositions comprising HMT and 3-isothiazolones.

19 Claims, No Drawings

USE OF HEXAMETHYLENETETRAMINE AS A STABILIZER FOR 3-ISOTHIAZOLONES

This is a continuation-in-part of U.S. Ser. No. 762,972, filed Sep. 20, 1991, (now abandoned), which is in turn a continuation of Ser. No. 07/488,350, filed Mar. 2, 1990, now abandoned.

BACKGROUND OF THE INVENTION

1. Field of the Invention

This invention concerns the stabilization of 3-isothiazolone compounds by the incorporation of hexamethylenetetramine with those compounds.

2. Description of the Prior Art

Isothiazolones have generated high commercial interest as microbicides to prevent spoilage of certain aqueous and non-aqueous products caused by microorganisms. Isothiazolones are highly effective microbicides (as used herein, "microbicides" includes bactericides, fungicides and algicides and microbicidal activity is intended to include both the elimination of and the inhibition or prevention of growth of microbial organisms such as bacteria, fungi and algae); by suitable choice of functional groups, they are useful in a broad range of applications. However, it has been long recognized that either in storage prior to addition to the substrate to be treated or after addition, their efficacy may be decreased because they are not stable under practical conditions of long-term storage. Means have thus been sought for some time to improve the stability of isothiazolones.

U.S. Pat. Nos. 3,870,795 and 4,067,878 teach the stabilization of isothiazolones against chemical decomposition by addition of a metal nitrite or metal nitrate, but teach that other common metal salts, including carbonates, sulfates, chlorates, perchlorates, and chlorides are ineffective in stabilizing solutions of isothiazolones, such solutions usually being in water or in an hydroxylic solvent.

U.S. Pat. Nos. 4,150,026 and 4,241,214 teach that metal salt complexes of isothiazolones are useful because they have enhanced thermal stability, while retaining biological activity.

It is known to use certain organic stabilizers for isothiazolones, generally for use situations where metal salts may create problems, such as corrosion, coagulation of latices, insolubility in non-aqueous media, interaction with the substrate to be stabilized, and the like. Formaldehyde or formaldehyde-releasing chemicals, e.g., quaternary salts of hexamethylenetetramine under basic conditions, are known as stabilizers, (see U.S. Pat. Nos. 4,165,318 and 4,129,448), as are certain organic chemicals such as orthoesters (U.S. application Ser. No. 118,366) and epoxides (U.S. application Ser. No. 194,234). Unlike its quaternary salts, hexamethylenetetramine has been shown to not release formaldehyde under basic conditions (H. W. Rossmore and M. Sondossi, "Advances in Applied Microbiology," 33,230 (1988)).

In certain applications, however, it is desirable to avoid addition of certain organic stabilizers by virtue of their volatility, decomposition under high heat, higher cost, difficulty in handling, potential toxicity, and the like.

In actual use, copper salts, such as copper sulfate, have proved efficacious in the stabilization of isothiazolones. However, copper salts may be undesirable in effluent streams in such operations as in the manufacture of stabilized isothiazolones or in their blending into a product or the use of that product. Copper salts, especially the chlorides, may contribute to possible corrosion, or in the presence of polymers in aqueous dispersion may lead to coagulation of the dispersion.

Japanese Kokai 54-132203 teaches the use of hexamethylenetetramine within a list of wood preservatives and benzisothiazolone within a list of fungicides as decorative board fungicidal systems; the Kokai does not disclose nor suggest the use of hexamethylenetetramine as a stabilizer for 3-isothiazolones, nor does it disclose 3-isothiazolones at all.

Hungarian Patent 46721 A2 discloses the use of hexamethylenetetramine as part of a fungicidal formulation for use in paint compositions; it also discloses the use of 2-octyl-3-isothiazolone as part of a primer formulation for use in paint compositions.

Japanese kokai 02-138102 discloses a marine antifouling paint formulation containing hexamethylenetetramine and 4,5-dichloro-2-octyl-3-isothiazolone in xylene. Non-hydroxylic solvents, such as xylene, do not require an additional stabilizer.

SUMMARY OF THE INVENTION

It is an object of the invention to provide a stabilization system for isothiazolones under basic conditions, i.e. above pH 7.0, which overcomes some or all of the disadvantages of prior art systems. It is also an object to provide an isothiazolone stabilized by only low levels of stabilizer so as to avoid interference with other components in systems in which isothiazolones are used as microbicides.

These objects, and others which will become apparent from the following disclosure, are achieved by the present invention. It has been surprisingly found that isothiazolones may be stabilized against decomposition by the addition of hexamethylenetetramine, hereinafter referred to as HMT, to the composition containing the isothiazolone. Accordingly the invention provides in one aspect a composition comprising:

a) at least one 3-isothiazolone of the formula (I)

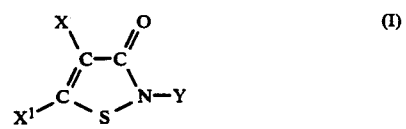

wherein
- Y is selected from the group consisting of hydrogen; alkyl or substituted alkyl of 1 to 18 carbon atoms; unsubstituted or halogen-substituted alkenyl or alkynyl of 2 to 8 carbon atoms; cycloalkyl or substituted cycloalkyl of 3 to 12 carbon atoms; aralkyl or halogen-, lower alkyl-, or lower alkoxy-substituted aralkyl of up to 10 carbon atoms; and aryl, halogen-, lower alkyl-, or lower alkoxy-substituted aryl of up to 10 carbon atoms; and
- X and $X^1$ are independently selected from the group consisting of hydrogen, halogen, and $(C_1-C_4)$alkyl;

b) hexamethylenetetramine (HMT); and c) water or hydroxylic solvent.

In another aspect, the invention comprises a method for inhibiting or preventing the growth of bacteria, fungi, yeast or algae in a locus subject or susceptible to contamination by bacteria, fungi, yeast or algae, which comprises incorporating onto or into the locus, in an amount which is effective to adversely affect the growth of bacteria, fungi, yeast, or algae, the aforementioned composition.

DETAILED DESCRIPTION OF THE INVENTION AND THE PREFERRED EMBODIMENTS

The 3-isothiazolones of interest include those disclosed in U.S. Pat. Nos. 3,523,121 and 3,761,488 as represented by the following formula:

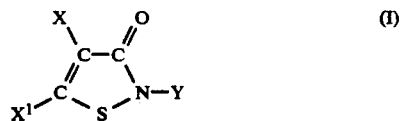

wherein Y is hydrogen; an alkyl or substituted alkyl of 1 to 18 carbon atoms, preferably from 4 to 10 carbon atoms; an unsubstituted or halogen substituted alkenyl or alkynyl of 2 to 8 carbon atoms, preferably from 2 to 4 carbon atoms; cycloalkyl or substituted cycloalkyl of 3 to 12 carbon atoms, preferably from 5 to 8 carbon atoms; an aralkyl or halogen-, lower alkyl-, or lower alkoxy-substituted aralkyl of up to 10 carbon atoms; or an aryl or halogen-, lower alkyl-, or lower alkoxy-substituted aryl of up to 10 carbon atoms; and X and $X^1$ are hydrogen, halogen, or a $(C_1-C_4)$alkyl.

Representative Y substituents include methyl, ethyl, propyl, isopropyl, butyl, hexyl, octyl, cyclohexyl, benzyl, 3,4-dichlorophenyl, 4-methoxybenzyl, 4-chlorobenzyl, 4-methoxyphenyl, 4-chlorophenyl, phenethyl, 2-(4-chlorophenyl)ethyl, hydroxymethyl, chloromethyl, chloropropyl, hydrogen, and the like.

Where the expression "lower" is employed in conjunction with terms, such as alkyl, alkoxy, etc., it is intended to indicate that the alkyl or alkyl portion thereof has 1 to 4 carbon atoms, i.e., $(C_1-C_4)$.

By a substituted alkyl group is meant an alkyl group having one or more of its hydrogen atoms replaced by another substituted group. Examples of the substituted alkyl groups which characterize 3-isothiazolones of this invention include hydroxyalkyl, haloalkyl, cyanoalkyl, alkylaminoalkyl, dialkylaminoalkyl, arylaminoalkyl, carboxyalkyl, carbalkoxyalkyl, alkoxyalkyl, aryloxyalkyl, alkylthioalkyl, arylthioalkyl, haloalkoxyalkyl, cycloalkylaminoalkyl, such as morpholinoalkyl, piperidinoalkyl, pyrrolidonylalkyl, and the like, carbamoxyalkyl, alkenyl, haloalkenyl, alkynyl, haloalkynyl, isothiazolonylalkyl, and the like.

By a substituted aralkyl group is meant an aralkyl group having one or more of the hydrogen atoms on either the aryl ring of the alkyl chain replaced by another substituent group. Examples of the substituent aralkyl groups which characterize 3-isthiaozlones of this invention include halogen-, lower alkyl-, or lower alkoxy-substituted aralkyl groups, and the like.

By a substituted aryl group is meant an aryl group, such as benzene, naphthalene, or pyridine, having one or more of the hydrogen atoms on the aryl ring replaced by another substitutent group. Examples of such substitutent groups include halogen, nitro, lower alkyl, lower alkyl-acylamino, lower carbalkoxy, sulfamyl, and the like.

Particularly preferred isothiazolones are 5-chloro-2-methyl-3-isothiazolone, 2-methyl-3-isothiazolone, 2-n-octyl-3-isothiazolone, 4,5-dichloro-2-cyclohexyl-3-isothiazolone and 4,5-dichloro-2-octyl-3-isothiazolone.

Most preferred is 5-chloro-2-methyl-3-isothiazolone, either as a sole compound or in admixture with 2-methyl-3-isothiazolone. When in admixture, the preferred ratio of monochlorinated/unchlorinated isothiazolone is from about 70:30 to about 85:15, and an especially preferred ratio is from about 70:30 to about 80:20. A second especially preferred isothiazolone is 2-methyl-3-isothiazolone in combination with low levels of 5-chloro-2-methyl-3-isothiazolone, a preferred ratio being from about 98:2 to about 96:4, and an especially preferred ratio being about 97:3. A third especially preferred isothiazolone is 2-n-octyl-3-isothiazolone.

The composition may contain from about 0.00001 to about 99 parts of the one or more isothiazolones, and from about 0.00001 to about 99 parts of HMT.

Generally, the composition of the invention will be in the form of a solution. Typical formulation ranges are illustrated in the following Table (all percentages are parts by weight) for both a concentrated solution of the isothiazolone and a dilute solution. For certain uses, such as shipping of large quantities, more concentrated solutions may also be utilized.

| FORMULATIONS TABLE | | |
|---|---|---|
| Isothiazolone (I, Supra) | HMT | Solvent |
| 0.00001–99% | 0.00001–99% Preferred | 0–99.99998% |
| 0.00001–5% | 0.00001–5% Most Preferred | 90–99.99998% |
| 0.0001–1% | 0.0001–1% | 98–99.9998% |

Solvents may be used to dissolve the isothiazolones and may be any organic solvent which dissolves the isothiazolones, is compatible with the proposed end use, does not destabilize the isothiazolone, and does not react with the HMT to eliminate its stabilizing action.

Water or hydroxylic solvents, for example, polyols, such as glycols, alcohols and the like, may be used. Under conditions of high dilution and high ratios of stabilizer to isothiazolone, glycols may be successfully used.

Preferred solvents are capped polyols, wherein the free hydroxyl group is replaced with an ether or ester function. Especially preferred are 2,5,8,11-tetraoxadodecane, commonly known as triethylene glycol dimethyl ether, and 4,7-dioxaundecanol-1 acetate, commonly known as diethylene glycol butyl ether acetate.

Water is a solvent for certain of the preferred isothiazolones and the HMT may be employed in aqueous formulations.

The amounts of HMT employed will vary depending on use conditions and concentrations of the isothiazolone in the mixture: effective amounts of HMT based on isothiazolone may be ratios in the range of from about 1:100 to about 1000:1 stabilizer to isothiazolone. In concentrated solutions, ratios are generally from about 1:50 to about 50:1. Obviously higher amounts may be used, but at additional cost. At high levels of dilution of the isothiazolone (such as from 1 to 10,000 ppm (0.0001–1%) isothiazolone in the solvent), the ratio of stabilizer to isothiazolone can range from about 1:10 to about 20:1. The preferred range is from 1:1 to 20:1.

The stabilization advantages of the HMT of the present invention are noted even when the isothiazolone contains other salt stabilizers recorded in U.S. Pat. Nos. 3,870,795, 4,067,878, 4,150,026 and 4,241,214.

Uses of these new organically stabilized microbicides are typically at any locus subject to contamination by bacteria, fungi, yeast or algae. Typically loci are in aqueous systems such as water cooling, laundry wash water, oil systems such as cutting oils, oil fields and the like where microorganisms need to be killed or where their growth needs to be controlled. However these stabilized microbicides may also be used in all applications for which known microbicidal compositions are useful; preferred utilities of the compositions are to protect wood paint, adhesive, glue, paper, textile, leather, plastics, cardboard, lubricants, cosmetics, food, caulking, feed and industrial cooling water from microorganisms. The loci composition must be basic, i.e., have a pH above 7.

The following lists typical industries and applications of compositions:

| Industry | Application |
| --- | --- |
| Adhesives, Sealants | adhesives |
|  | caulks |
|  | sealants |
| Agriculture/food chain | adjuvant preservation |
|  | agricultural active ingredient |
|  | agricultural chemical preservative |
|  | agricultural formulations preservation |
|  | animal feed preservation |
|  | dairy chemicals |
|  | fertilizer preservation |
|  | food preservation |
|  | food processing chemicals |
|  | grain preservation |
|  | post-harvest produce protection |
|  | sugar processing |
|  | tobacco |
| Construction products | asphalt/concrete |
|  | cement modifiers |
|  | construction products |
|  | roof mastics |
|  | synthetic stucco |
|  | wall mastics |
|  | joint cement |
| Cosmetics and toiletries | cosmetics |
|  | raw materials for cosmetics, toiletries |
|  | toiletries |
| Disinfectants, antiseptics | antiseptic |
|  | disinfectant |
| Emulsions, dispersions | aqueous dispersions |
|  | dispersed pigments |
|  | latex |
|  | photographic emulsions |
|  | pigment slurries |
|  | polymer latices |
| Formulated consumer and industrial products | air fresheners |
|  | fabric softeners |
|  | polishes, floor, furniture, shoe |
|  | waxes |
|  | hand cleaners |
|  | sponges and towelettes |
|  | spray starch |
|  | waxes |
| Industrial processing, misc | electrodeposition paint, baths, rinses. |
|  | electrodeposition pre-treatment, post rinses |
|  | industrial fluids preservation |
|  | pasteurization baths |
|  | process aid preservation |
| Industrial water treatment | air washers |
|  | cooling towers |
|  | cooling water |
|  | water cooling |
|  | preservation/treatment of wooden cooling tower slats and structural members |
|  | can warmers |
|  | brewery pasteurization |
|  | closed loop water cooling systems |
| Laundry | household laundry products |
|  | laundered goods |
|  | laundry [wash] rinse water |
|  | sanitizers-laundry |
| Leather, leather products | leather and hide |
|  | leather and hide products |
| Lubricants, hydraulic aids | automotive lubricants and fluids |
|  | conveyor lubricants |
|  | greases |
|  | hydraulic fluids |
|  | lubricants |
| Medical devices | diagnostic enzymes |
|  | diagnostic kits |
|  | medical devices |
| Metalworking & related app's | cutting fluids |
|  | metal cleaning |
|  | metalworking fluids |
| Odor control (active ingredient) | air conditioning |
|  | animal bedding |
|  | cat litter |
|  | chemical toilet prep'ns |
|  | deodorizers |
|  | humidifiers |
|  | industrial deodorants |
|  | sanitary formulations |
|  | toilet bowls |
| Paints and coatings | emulsions |
|  | paints |
| Paper and wood pulp, their products | absorbant materials of paper and wood pulp |
|  | packaging materials of paper and wood pulp |
|  | paper |
|  | paper products |
|  | paper treatment |
|  | soap wrap |
|  | wood pulp |
|  | wood pulp products |
| Paper mill | paper mill slimicides |
|  | pulp and paper slurries |
| Petroleum refining, fuels | aviation fuels (jet fuel, aviation gas) |
|  | crude oils |
|  | burner, diesel and turbine fuel oils |
|  | coal slurries |
|  | diesel fuel additives |
|  | diesel fuels |
|  | fuels |
|  | gasoline |
|  | heating oils |
|  | hydrocarbons |
|  | kerosene |
|  | liquefied petroleum gas |
|  | petrochemical feedstocks |
|  | petroleum products, storage, transportation and production |
|  | recycled petroleum products |
|  | residual fuel oils |
|  | turbine oils |
| Photographic chemicals | photographic processing - wash water, and process rinses |
|  | photoprocessing |
|  | photoplate processing chemicals (developers, stabilizers etc) |
| Printing | fountain solutions (printing) |
|  | ink components (pigments, resins, solvents, etc) |
|  | inks |
| Sanitizers (active) | sanitizers |
|  | sanitizer-dairy |
|  | sanitizers-dental |
|  | sanitizers-fermentation |
|  | sanitizers-food preparation |
|  | sanitizers-food processing |
|  | sanitizers-medical |
|  | sanitizers-rendering |
|  | sanitizers-veterinary |
| Soaps, detergents, cleaners | cleaners |
|  | detergents |
|  | household cleaners |
|  | industrial cleaners |
|  | liquid soaps |
|  | oil and grease remover |

| Industry | Application |
| --- | --- |
| | powdered soaps |
| | raw materials for cleaning products |
| | soaps |
| | surfactants |
| Textiles, textile products | bonded fabrics |
| | burlap |
| | canvas |
| | canvas goods |
| | carpet backing |
| | carpets |
| | clothing |
| | coated fabrics |
| | curtains |
| | draperies |
| | engineering textiles |
| | fibers |
| | geotextiles |
| | goods made of textiles |
| | knitted fabrics |
| | nets |
| | nonwoven fabrics |
| | rope |
| | rugs |
| | textile accessories |
| | textile products |
| | textiles |
| | upholstery |
| | woven fabrics |
| | yarn |
| Textile processing | dye fixatives |
| | dyes |
| | fiber lubricants |
| | hand modifiers |
| | sizes |
| | textile processing fluids |
| Therapeutic (active or preservative) | animal health/veterinary |
| | aquaculture |
| | dental |
| | human health |
| | pharmaceutical/therapeutic |
| Water purification | charcoal beds |
| | deionization resins |
| | filters |
| | membranes |
| | reverse osmosis membranes |
| | ultrafilters |
| | water purification |
| | water purification pipes, tubing |
| Wood applications | lazures (wood stains) |
| | wood |
| | wood products |
| Miscellaneous | alcohols |
| | bedding incorporating water or gels |
| | ceramic |
| | contact lens cases-leaching |
| | electronic circuitry |
| | electronics chemicals |
| | enzymes-food production |
| | enzymes |
| | enzymes-industrial |
| | gel cushions |
| | marine antifoulants |
| | mildewcides |
| | wood |
| | plastics |
| | laundry |
| | mining |
| | natural rubber latex |
| | oil field injection waters including enhanced recover injection fluids, drilling, fracturing and completion fluids |
| | pipes |
| | plastics |
| | polymer systems |
| | polymers and resins (synthetic and natural) |
| | reagent preservation |
| | rubber |
| | rubber products |
| | skin remover |
| | solid protective/decorative films |
| | stains |
| | swimming pools |
| | waste treatment |
| | water beds |

Because isothiazolones are so active as microbicides and only low levels of HMT are required to achieve stabilization, the amount of HMT in systems being treated will be very small, and therefore it is not likely to interfere with other components in systems requiring protection or with systems to which the protected systems will be applied. Potential areas of general application include metal-working fluids, paints, cooling water, and air washers.

One significant area of application for the compositions of the invention is as microbicides in metal working fluids. Metal working fluids are proprietary combinations of chemicals, which may contain, inter alia, ingredients such as alkanolamines, petroleum sulfonate surfactants, oils (naphthenic, paraffinic, etc.), chlorinated paraffins and fatty esters, sulfurized fatty compounds, phosphate esters, fatty acids and their amine salts, glycols, polyglycols, boric acid esters and amides. They are utilized in the milling, machining, drilling, and other processing technologies for fabricating metal for the purposes of lubricating, cooling, preventing surface corrosion, and the like. They are sold in the form of active metal working fluid (MWF) concentrates, and are diluted in use to 1–10% active ingredients in water.

Because metal working fluids are recycled and stored, the growth of microorganisms is favored. Isothiazolones have been found effective in preventing the growth of such organisms. Certain of the components in the metal working fluids will tend to destroy the isothiazolone and so remove its microbicidal protective activity, so that stabilizers for the isothiazolone against such degradation are desirable.

It is known in the art that the performance of microbicides may be enhanced by combination with one or more other microbicides. Thus, other known microbicides may be combined advantageously with the composition of this invention.

The following examples are intended to illustrate the present invention and not to limit it except as it is limited by the claims. All percentages are by weight unless otherwise specified, and all reagents are of good commercial quality unless otherwise specified. Methods for quantitative determination of the isothiazolones in the following examples in metal-working fluids are described in detail in "Kathon ® 886 MW Microbicide and Kathon ® 893 MW Fungicide: Analysis in Metalworking Fluids by High-Performance Liquid Chromatography", 1988, Rohm and Haas Company.

EXAMPLE 1

These examples demonstrate the stabilizing effect of HMT for isothiazolones added to a metal working fluid (MWF). MWF concentrate A was a "semi-synthetic" type having about 10 to 15 percent naphthenic/paraffinic oil, about 50 percent water, emulsifying agents, pH adjusting amines, anticorrosive agents, and EP (extreme pressure) agents. The pH of MWF concentrate A was measured and found to be 9.0.

Into a glass vial in the following order were placed: a) 5 parts by weight of the MWF concentrate solution, b) 5 parts of the stabilizer in solution or dispersion, c) 5 parts water, d) 5 parts of an aqueous solution containing 80 ppm active ingredient (AI), prepared by dilution of a 14.4% aqueous solution of an approximately 75/25 mixture of 5-chloro-2-methyl-3-isothiazolone and 2-methyl-3-isothiazolone; also present was 9.2% magnesium chloride and 15.7% magnesium nitrate. Thus the final mixture contained 3-5% of the MWF concentrate, 20 ppm active ingredient of the isothiazolone, and 0 (control) to 2,000 ppm of the stabilizer.

The vials were then capped, stored at ambient room temperature in a closed cabinet for a designated time, filtered through a 0.45 micron filter into another vial and analyzed the same day. The relative concentration of the active ingredient was determined by reverse phase high pressure liquid chromatography, utilizing a Varian model 5500 chromatograph and an ultraviolet detector. Results of this study are found in Table 1.

TABLE 1

MWF A STABILIZED WITH HEXAMETHYLENETETRAMINE AGED 4 DAYS

| HMT Level (ppm) | % AI remaining |
|---|---|
| 0 | 40 |
| 50 | 59 |
| 100 | 62 |
| 200 | 67 |
| 500 | 70 |
| 1000 | 71 |
| 2000 | 71 |

EXAMPLE 2

This example illustrates the ability of HMT to be used in stabilization of isothiazolones used as mildewcides in paint formulations. The water-based paint formulation was prepared from standard ingredients, utilizing a commercial acrylic-based latex with conventional pigments, dispersants, and the like. The pH of the paint formulation was measured and found to be 9.5.

To two sealable containers were charged 100 parts of the paint formulation. To one was charged twice the desired final stabilizer concentration, and to the other, twice the desired isothiazolone concentration. Both portions were homogenized for 15 minutes each, then blended and re-mixed. The sealed containers were stored at 60° C. and samples were removed at 0 and 15 days.

To 1 part of the sample was added 9 parts propylene glycol, the diluted sample shaken for one hour, centrifuged at 70,000 rpm for 30 minutes, the supernatant diluted with two volumes of methanol, and that solution filtered through a 0.45 micron filter. The filtered sample was injected directly into the HPLC described in Example 1. Appropriate analytical calibrations were made for the 2-octyl-3-isothiazolone studied. The 2-octyl-3-isothiazolone was added as a 45.5 wt. % solution in propylene glycol. The following formulation is a typical paint blend for testing of stabilization against microbial activity. Texanol ® is trimethyl-1,3-pentanediol monoisobutyrate supplied by Eastman Chemical. "Latex" is a latex of a copolymer of butyl acrylate and methyl methacrylate.

TABLE 2

LATEX PAINT FORMULATION

| Material | lb/50 gal | g/l |
|---|---|---|
| Natrosol 250 MHR hydroxyethyl cellulose | 1.5 | 3.6 |
| Ethylene glycol | 12.5 | 30 |
| Premix | | |
| Water | 56.0 | 134.4 |
| Tamol 960 (40%) poly(methacrylic acid) | 3.6 | 8.6 |
| Potassium tripolyphosphate | 0.75 | 1.8 |
| Triton CF-10 surfactant | 1.3 | 3.1 |
| Colloid 643 thickener | 0.5 | 1.2 |
| Propylene glycol | 17.0 | 40.8 |
| Ti-Pure R-902 titanium dioxide | 112.5 | 270 |
| Minex 4 filler pigment | 79.7 | 191.3 |
| Icecap K filler pigment | 25.0 | 60 |
| Attagel 50 clay | 2.5 | 6 |
| Let Down | | |
| Latex | 153.0 | 367.1 |
| Colloid 643 | 1.5 | 3.6 |
| Texanol coalescent | 4.7 | 11.3 |
| Ammonia (28%) | 1.16 | 2.8 |
| Natrosol 250 MHR (2.5%) | 53.50 | 128.4 |
| Water | 54.46 | 130.8 |
| | 581.17 | 1394.9 |

In Table 3 are presented results for 15 days aging at 60° C.

TABLE 3

LATEX PAINT CONTAINING 2-OCTYL-3-ISOTHIAZOLONE PRESERVATIVE PLUS HMT STABILIZER

| Preservative, ppm | ppm HMT | % AI Remaining |
|---|---|---|
| 1600 | 0 | 3 |
| 1600 | 1000 | 100 |

I claim:
1. Composition comprising
a) a bactericidal, algicidal or fungicidal effective amount of at least one 3-isothiazolone of the formula (I)

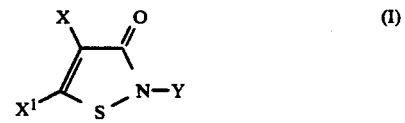

wherein
Y is selected from the group consisting of hydrogen; alkyl or substituted alkyl of 1 to 18 carbon atoms; unsubstituted or halogen-substituted alkenyl or alkynyl of 2 to 8 carbon atoms; cycloalkyl or substituted cycloalkyl of 3 to 12 carbon atoms; aralkyl or halogen-, lower alkyl-, or lower alkoxy-substituted aralkyl of up to 10 carbon atoms; and aryl, halogen-, lower alkyl-, or lower alkoxy-substituted aryl of up to 10 carbon atoms; and X and $X^1$ are independently selected from the group consisting of hydrogen, halogen, and ($C_1$-$C_4$)alkyl;

b) a stabilizing effective amount of hexamethylenetetramine (HMT); and c) water or hydroxylic solvent provided that when water is present, the pH of the composition is above pH 7.

2. Composition according to claim 1 wherein one or more of each 3-isothiazolone is selected from the group consisting of 5-chloro-2-methyl-3-isothiazolone, 2- methyl-3-isothiazolone, 2-n-octyl-3-isothiazolone, 4,5-dichloro-2-cyclohexyl-3-isothiazolone, and 4,5-dichloro-2-octyl-3-isothiazolone.

3. Composition according to claim 1 comprising HMT and a mixture of 5-chloro-2-methyl-3-isothiazolone and 2-methyl-3-isothiazolone.

4. Composition according to claim 1 comprising HMT and 2-n-octyl-3-isothiazolone.

5. Composition according to claim 1 wherein the 3-isothiazolone comprises about 0.00001 to about 99% by weight, the HMT comprises about 0.0001 to about 99% by weight and which further comprises up to about 99.99998% by weight of solvent.

6. Composition according to claim 1 wherein the 3-isothiazolone comprises about 0.00001 to about 5% by weight, the HMT comprises about 0.00001 to about 5% by weight, and solvent comprises about 90 to about 99.99998% by weight.

7. Composition according to claim 1 wherein the 3-isothiazolone comprises about from 0.0001 to about 1% by weight, the HMT comprises about 0.0001 to about 1% by weight, and solvent comprises about 98 to about 99.9998% by weight.

8. Composition according to claim 1 wherein the ratio of HMT to 3-isothiazolone is about 1:50 to about 20:1 by weight.

9. Composition according to claim 1 wherein the ratio of HMT to 3-isothiazolone is about 1:1 to about 20:1 by weight.

10. Composition according to claim 1 wherein said hydroxylic solvent is selected from alcohols, polyols and glycols.

11. Composition according to claim 10 wherein said hydroxylic solvent is a capped polyol.

12. Composition according to claim 11 wherein said capped polyol is selected from 2,5,8,11-tetraoxadodecane and 4,7-dioxaundecanol-1 acetate.

13. Composition comprising latex paint comprising as the mildewcide a mildewcide composition according to claim 1, said latex paint composition having a pH greater than 7.

14. Composition comprising metal working fluid comprising as the microbicide a microbicidal composition according to claim 1, said metal working fluid composition having a pH greater than 7.

15. A method of stabilizing a compound of the formula I

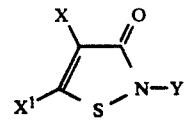

wherein
Y is selected from the group consisting of hydrogen; alkyl or substituted alkyl of 1 to 18 carbon atoms; unsubstituted or halogen-substituted alkenyl or alkynyl of 2 to 8 carbon atoms; cycloalkyl or substituted cycloalkyl of 3 to 12 carbon atoms; aralkyl or halogen-, lower alkyl-, or lower alkoxy-substituted aralkyl of up to 10 carbon atoms; and aryl, halogen-, lower alkyl-, or lower alkoxy-substituted aryl of up to 10 carbon atoms; and
X and $X^1$ are independently selected from the group consisting of hydrogen, halogen, and (C1–C4)alkyl;

comprising incorporating an effective stabilizing amount of HMT provided that when water is present, the pH of the composition is above pH 7.

16. Method according to claim 15 wherein the ratio of incorporated HMT to 3-isothiazolone present is from about 1:100 to 1000:1.

17. Method according to claim 16 wherein the ratio of incorporated HMT to 3-isothiazolone present is from about 1:50 to 20:1.

18. Method of inhibiting or preventing the growth of bacteria, fungi or algae in a locus subject or susceptible to contamination thereby, comprising incorporating into or onto the locus a composition according to claim 1 in an amount effective to adversely affect the growth of said bacteria, fungi or algae.

19. Method according to claim 18 wherein the locus is selected from a metal-working fluid, a cutting oil, a water-cooling system, a cosmetic formulation, a paint, and a film-forming agent.

* * * * *